United States Patent [19]

Ahsbahs et al.

[11] Patent Number: 4,784,145
[45] Date of Patent: Nov. 15, 1988

[54] MEMBRANE RETAINER ASSEMBLY FOR PHYSIOLOGICAL SENSING UNITS

[75] Inventors: Walter Ahsbahs, Merzhausen; Karl-Heinz Pomorin, Stegen; Helmut Leist, Waldkirch; Georg Ullrich, Freiburg, all of Fed. Rep. of Germany

[73] Assignee: Hellige GmbH, Freiburg, Fed. Rep. of Germany

[21] Appl. No.: 26,088

[22] Filed: Mar. 16, 1987

[30] Foreign Application Priority Data

Mar. 18, 1986 [DE] Fed. Rep. of Germany ....... 3609080

[51] Int. Cl.⁴ ................................................ A61B 5/00
[52] U.S. Cl. .................................... 128/635; 204/415
[58] Field of Search ................. 128/635; 204/403, 415

[56] References Cited

U.S. PATENT DOCUMENTS

| 4,273,134 | 6/1981 | Ricciardelli | 128/635 |
| 4,303,076 | 12/1981 | Danek | 128/635 |
| 4,425,918 | 1/1984 | Moll et al. | 128/635 |

FOREIGN PATENT DOCUMENTS 3111191 11/1982 Fed. Rep. of Germany .

Primary Examiner—Lee S. Cohen
Attorney, Agent, or Firm—Edward J. Whitfield

[57] ABSTRACT

Disclosed herein is a retainer assembly for applying a membrane to a physiological sensing unit for the transcutaneous determination of the magnitude of physiological quantities, particularly for measuring the partial pressure of gases in blood or the like. The assembly constitutes a preassembly of a membrane, with a clamping ring accommodating the membrane and having an annular recess receiving the rim of the membrane. The clamping ring has a lip in the form of an inwardly protruding annular edge for removably securing the clamping ring together with the membrane to the sensing unit by virtue of the lip resiliently snapping into a peripheral groove of the sensing unit, the lip defining the periphery of the annular recess. A retainer element is provided for temporarily and removably assembling the membrane with the clamping ring prior to assembly with the sensing unit. The retainer element includes a retaining ring fitted loosely into the annular recess of the clamping ring, to maintain the outer rim of the membrane within the annular recess.

In accordance with a preferred embodiment of the invention, the retaining ring is provided with at least one radially inwardly extending tongue-like tab formed integrally with and of the same material as the retaining ring. When the assembly is secured to the sensing unit, the tongue-like tab functions so as to provide a capillary connection between the atmosphere and the electrolyte film disposed between the membrane and the measuring surface of the sensing unit to eliminate fluctuations in electrolyte film thickness caused by water vapor diffusing through the membrane and into the electrolyte.

5 Claims, 2 Drawing Sheets

MEMBRANE RETAINER ASSEMBLY FOR PHYSIOLOGICAL SENSING UNITS

FIELD OF THE INVENTION

This invention relates to an improved retainer assembly for positioning and retaining a membrane in contact with the measuring surface of a physiological sensing unit.

BACKGROUND OF THE INVENTION

Physiological sensing units of the electrochemical type are commonly used for non-invasive transcutaneous measurement of partial pressure of gases, e.g., oxygen and carbon dioxide, in blood and body tissue. Exemplary of such electrochemical sensors are those of the Clark type typically used for polarographic oxygen measurement and those of the Stow-Gertz-Severinghaus type typically used for ion-sensitive carbon dioxide measurement. In operation, a membrane is uniformly and tautly stretched over the measuring surface of the sensing unit, with a very thin film of hygroscopic electrolyte uniformly disposed between the measuring surface and the membrane. The membrane is positioned and retained in contact with the measuring surface by a removable retaining assembly such as the assembly described in commonly owned U.S. Pat. No. 4,425,918, which assembly has gained acceptance in the industry and has proved to be quite commercially successful.

A particular problem associated with such physiological sensors is, that during use, water vapor can diffuse through the outer surface of the diaphragm and into the electrolyte film which water vapor increases the film thickness resulting in undesirable effects, particularly, an increase in the diffusion resistance of the gas being measured as well as an increase in the conductance of the electrolyte. Consequently, the sensitivity of the sensor can be adversely affected and response time to changes in gas concentration can be unduly prolonged.

In order to avoid such change in film thickness of the electrolyte, the sensor element itself could be provided with compensating capillaries or channels which, for example, could be incorporated into the encircling mating-surface rim. On the one hand, however, this is not possible with respect to sensors already in the field. On the other hand, relatively thick capillaries would be required in order to maintain function when wear is caused by repeated covering and despite unavoidable depositing, for example, of electrolyte residues. Also, in state of the art measuring sensors, this could in turn promote premature migration of the electrolyte.

OBJECT OF THE INVENTION

The principal object of this invention is to provide a removable retainer ring assembly for positioning and retaining a membrane in contact with the measuring surface of a physiological sensing unit which retainer assembly is an improvement over the retainer assembly disclosed in U.S. Pat. No. 4,425,918 which improved retainer assembly affords the advantage of avoiding undesirable changes in the film thickness of the hygroscopic electrolyte disposed between the measuring surface of the sensor and the membrane.

DESCRIPTION OF THE DRAWINGS

The foregoing object and other advantageous details will become apparent from the following description of an exemplary embodiment of the invention illustrated by the following drawings in which.

DESCRIPTION OF THE INVENTION

Figure 1:
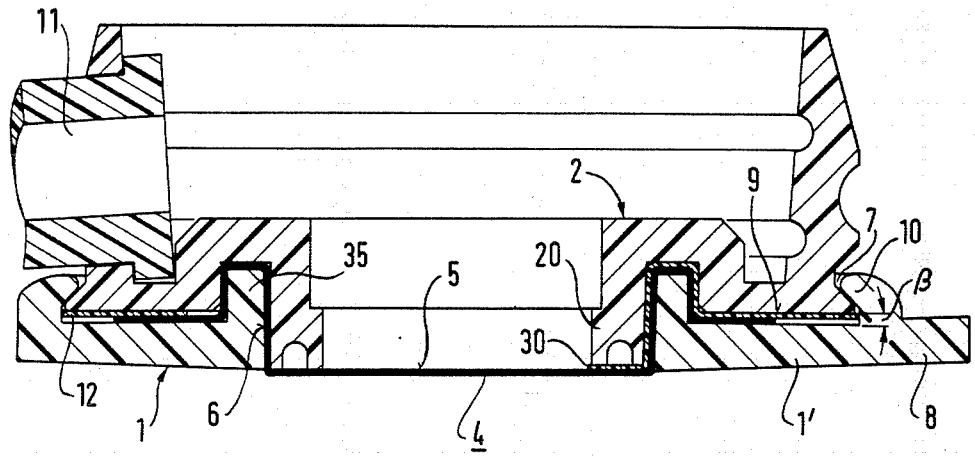
FIG. 1 is a sectional view through the housing of a physiological sensor unit having the improved retainer assembly of the invention releasably secured thereto.

FIG. 1 shows a housing main body 2 of a physiological sensing unit with lateral signal delivery via a cable 11. The construction of the detector, i.e., the sensing element proper, is in accordance with conventional technology and therefore, does not require any further explanation herein. The measuring surface 5 of the sensing unit, defined as the area within a downwardly projecting peripheral edge 20 of the housing main body 2, is covered by a circular membrane 4 of thin film material, made for example of the plastic material polytetrafluoroethylene (known under the trade name "Teflon"), or of polypropylene or polyethylene, and which appears essentially thicker in the diagrammatic view than corresponds to the actual proportions. The drawing illustrates the sensing unit in a view enlarged about ten times.

FIG. 1 shows the membrane 4 which covers the measuring surface 5 and which is kept stretched mainly at the mating surface 6 by the clamping ring 1. The clamping ring 1 itself is assembled with the housing 2 by means of a lip in the form of a retaining edge 10 which is slightly bent to protrude inwardly at its outer edge, as the lip engages a peripheral groove 7 in the lower outer surface area of the housing 2. The outer edge of the clamping ring 1 may be provided with a gripping handle or tab 8 by which the clamping ring 1 can easily be removed when a membrane change is necessary.

Figure 2:
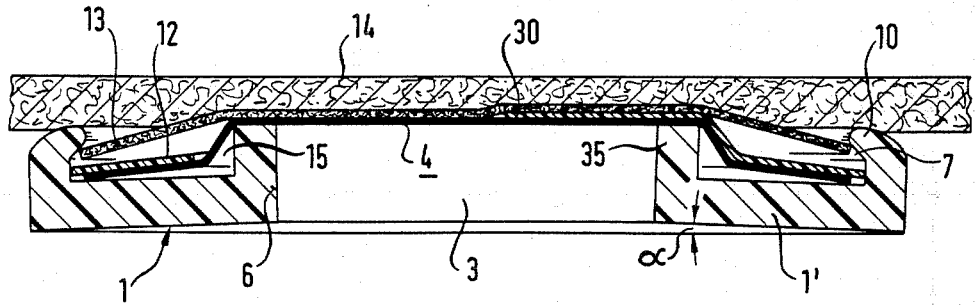
FIG. 2 is a sectional view through a preassembly of the improved retaining assembly of the invention prior to its being releasably secured to the sensor unit.

FIG. 2 shows the clamping ring preassembly as an exchangeable spare part. As illustrated, the open central space of the clamping ring is covered on the top side by the membrane 4. The membrane 4 is loosely fitted into the annular recess 15 of the clamping ring, as shown, the lip deforming the periphery of the annular recess. The outer rim of the membrane 4 is maintained within the recess 15 of the clamping ring 1 by a retaining ring 12 which is inserted from the top into the annular recess 15. The recess is defined between the inwardly bent retaining edge forming lip 10 and the clamping wall surface of the clamping ring 1. The retaining ring 12 covers the peripheral outer rim of the membrane 4. Its outside diameter is dimensioned so that it fits under slight pressure below the retaining edge or lip 10 on the inside of the lip and retains the membrane 4 and holds it taut.

On its upper side, the membrane 4 is covered by a protective film disc 13 which is suitably a round disc of stiff paper with an outside diameter which is likewise slightly greater than the diameter of the clamping ring at the upper, inner periphery of the lip, i.e., retaining edge 10. The protective film disc 13 thus likewise engages beneath the lip 10, so that the delicate film material constituting the membrane 4 is protected on its upper side.

A protective retaining bond 14, conveniently referred to as a backing strip, serves to facilitate handling and storing several preassemblies of retaining rings provided with membranes. A self-adhesive coating upon band 14 into which, as FIG. 2 reveals, the clamping ring 1 with the protective film disc 13 can be lightly pressed may constitute a common support for a plurality of preassemblies, inasmuch as the self-adhesive coating of the protective retaining band 14 adheres firmly to the upper edge of the lip 10 and also to the outer surface of the protective film disc 13 with relatively slight adhesive action. In the view of FIG. 2, the gripping bar or tab 8 is not shown.

The foregoing description is conventional and relates to the retaining assembly described in U.S. Pat. No. 4,425,918.

Figure 3:
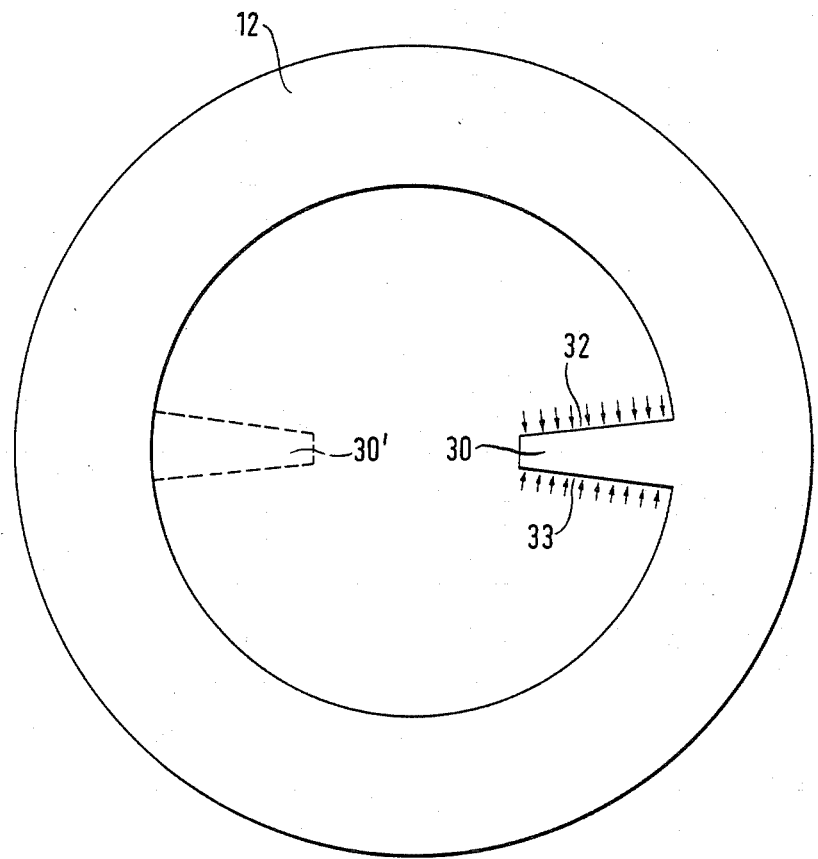
FIG. 3 is a plan view of the retaining ring showing the preferred embodiment of the improvement of this invention.

According to the preferred embodiment of the improvement of this invention as illustrated in FIG. 3, the retaining ring 12 is provided with at least one radially inwardly extending, tongue-like tab 30 which is formed integrally with and of the same material as retaining ring 30. Of course, a plurality of such tongue-like tabs may be Provided, one other of which 30' is indicated by broken lines. As shown in FIG. 2, the tongue-like tab 30 extends between the membrane 4 and the protective disc 13, that is, when the retaining assembly has not yet been secured to the measuring sensor 1, which protective disc 13 covers the membrane on the upper side and is typically made of stiff paper with an outside diameter which is likewise slightly larger than the diameter of the clamping ring at the upper encircling inner edge of the retaining rim 10. The disc 13, therefore, likewise snaps in beneath the retaining rim 10, so that the extremely thin foil of the membrane 4 is protected on the upper side.

As FIG. 1 illustrates, when the clamping ring 1 is snapped onto the measuring sensor, the tongue-like tab 30 lies between the membrane 4, now stretched taut, and the mating-surface rim 6. The length of the tongue-like tab 30 is of such a size that when the measuring sensor is covered with the membrane 4, it extends from the outer rim of the measuring surface 5 over the entire mating surface 6, of slightly tapered configuration, up to the undersurface 9 at the base body 2, that is into the area of the intermediate gap between the undersurface 9 of the base body 9 and the outer annular flange 1' of the clamping ring 1. The retaining ring 12, in the covered condition of the measuring sensor, remains in this intermediate gap, indicated by the reference symbol B.

The tongue-like tab 30 provided according to the invention has the following effect:

As mentioned above, the film thickness of the hygroscopic electrolyte between the measuring surface 5 and the membrane 4 can change on account of water diffusing through the membrane, with the attendant disadvantages resulting therefrom as affecting function of the measuring sensor. The tongue-like tab 30 according to the invention now has the effect that capillary-like channels 32 and 33 form between the diaphragm 4 and the encircling mating-surface rim 6, which channels 32 and 33 are indicated in FIG. 3 by small arrows. These capillary channels 32 and 33 develop because the diaphragm 4, in the area of the tongue-like tab 30, no longer bears in fully sealing manner against the mating-surface rim 6, at least when the internal pressure is increasing slightly.

The cross-section of the capillary channels 32 and 33 is exceptionally fine and can otherwise be determined first of all by the width and the section of the tongue-like tab 30, but above all by suitable selection of the material thickness for the retaining ring 12. This retaining ring 12 is made of a chemically neutral, thin foil material, for example of polyester foil material with a film thickness of from about 5 to about 500 microns, preferably from about 25 to about 100 microns. In a proven embodiment of the invention a material film thickness of 50 microns was selected for the retaining ring 12. In order not to impair the measured result, the tip of the tongue-like tab 30 should reach just up to the outer rim of the measuring surface 5, that is, it should not cover or impinge on any significant portion of the measuring surface.

As already known from U.S. Pat. No. 4,425,918, a self-adhesive protective and retaining strip 14 is used for the better handling and preservation of several retaining rings provided with a membrane. For changing a diaphragm 4 on the measuring sensor, the following procedure is used:

The clamping ring 1, with the membrane 4 secured and centered by the retaining ring 12, is removed from the protective, retaining strip 14, with the protective film disc 13 adhering to the strip 14. The clamping ring, with the diaphragm 4 already centered, is then fitted over the mating-surface rim 6, with the diaphragm 4 stretching tautly over the measuring surface 5 and being clamped on the mating-surface rim 6. At the same time, the tongue-like tab 30, as can be seen from FIG. 1, now lies between the clamping area of the diaphragm 4 and the mating-surface rim 6. In the area of its flange-like outer rim 1', the clamping ring 1 is pressed against the undersurface 9 of the measuring sensor housing 2, so that the lip 10 snaps into the peripheral groove 7. An additional stretching and clamping effect results from the flange-like outer rim 1' of the clamping ring 1 being inclined slightly from the inside outward in the non-stretched-on condition (angle a; cf. FIG. 2), by means of which, when the lip 10 engages into the peripheral groove 7, a pressure stress results on the undersurface of the housing 2. To further improve, i.e., increase the clamping action of the retainer assembly at the mating surface rim 6, the bearing surface 9 of the clamping ring 1 of the housing 2 may be beveled from the inside to the outside at an angle $\beta$ of 2° to 6°, preferably about 4° as shown in FIG. 1.

A simple, reliable means has been created by the invention in order to avoid, on account of water diffusing in and therefore an accompanying change in the film thickness of the electrolyte, falsifications in measured values in electrochemical sensors which work with a hygroscopic electrolyte. In the preferred embodiment of the invention, this is achieved by a modification of the retaining ring 12, the advantageous function of which is already described in U.S. Pat. No. 4,425,918. However, if another method of stretching and fixing the diaphragm over the measuring surface of the measuring sensor is provided, then the desired capillary action can also be achieved, without deviating from the concept of the invention, by a narrow strip of foil being inserted between the diaphragm and the mating surface at the base body of the measuring sensor. This can be effected, for example, in such a way that a narrow strip of foil is placed onto either the mating surface at the measuring sensor or the inner side of the diaphragm foil, with the bond being ensured as a rule by adhesion. However, since these strips of foil are tiny little pieces of a transparent, very thin foil material, practical handling difficulties result when inserting such a strip. In the described exemplary embodiment of the invention, however, such difficulties are completely avoided, since the tongue-like tab 30 is made in one piece with the retaining ring 12 and is automatically inserted in the correct position as soon as the diaphragm is stretched over the measuring surface 5 by pressing the clamping ring 1 onto the measuring sensor.

We claim:

1. An improved retainer assembly for positioning a membrane in contact with the measuring surface of electrochemical physiological sensing unit especially suited for transcutaneous measurement of partial pressure of gas in blood or body tissue reducing changes in electrolyte film thickness said assembly comprising:

a membrane;

a clamping ring having a central opening and a peripheral annular recess receiving the rim of the membrane such that the membrane spans the opening, the clamping ring also having an inwardly projecting annular lip adapted to resiliently engage an annular groove of the sensing unit whereby the clamping ring is removably secured to the sensing unit; and a retaining ring having a central opening, the rim of which is loosely fitted into the annular recess of the clamping ring thus maintaining the outer rim of the membrane within the annular recess, wherein the improvement resides in providing means in the form of at least one element selected from a foil strip or a tongue-like tab formed integrally with the retaining ring, said element extending radially inwardly from the rim of the retaining ring and so sized that when the retainer assembly is secured to the sensing unit the said element forms at least one capillary connection between the atmosphere and the electrolyte disposed between the membrane and the measuring surface of the sensing unit without the element itself covering or impinging on any significant portion of the measuring surface.

2. The improved retainer assembly of claim 1 wherein the retaining ring and tongue-like tab formed integrally therewith are fabricated of a chemically neutral foil material having a thickness of from about 5 to about 500 microns.

3. The improved retainer assembly of claim 1 including a removable self-adhesive backing material temporarily supporting at least one retainer assembly by adhesion to the lip of the clamping ring and to the central surface area surrounded by the lip.

4. The improved retainer assembly of claim 1 including a removable disc-like auxiliary retaining element disposed over the retaining ring, the rim of which disc being removably fitted into the annular recess of the clamping ring.

5. The improved retainer assembly of claim 4 including a removable self-adhesive backing material temporarily supporting at least one retainer assembly by adhesion to the outer surface of the disc-like auxiliary retaining element.

* * * * *